United States Patent [19]

Loosen et al.

[11] Patent Number: 5,278,333

[45] Date of Patent: Jan. 11, 1994

[54] PROCESS FOR THE ALPHA-MONOALKYLATION OF ARYLACETONITRILES, ARYLACETOESTERS AND ARYLACETIC ACIDS

[75] Inventors: Pierre C. Loosen, Tessenderlo, Belgium; Pietro Tundo; Maurizio Selva, both of Treviglio, Italy

[73] Assignee: Tessenderlo Chemie N.V., Stationsstraat-Tessenderlo, Belgium

[21] Appl. No.: 922,140

[22] Filed: Jul. 30, 1992

[30] Foreign Application Priority Data

Jul. 31, 1991 [IT]   Italy ........................... MI91A002137
Jan. 17, 1992 [IT]   Italy ........................... MI92A000081

[51] Int. Cl.$^5$ ................. C07C 253/30; C07C 69/157; C07D 333/24

[52] U.S. Cl. ........................ 562/52; 549/61; 549/65; 549/66; 549/71; 549/72; 549/74; 549/79; 560/53; 560/56; 560/100; 560/101; 560/102; 560/103

[58] Field of Search ............... 558/378, 371; 560/56, 560/102, 103, 52, 53, 56, 100, 101; 549/74, 79

[56] References Cited

U.S. PATENT DOCUMENTS

| | | | |
|---|---|---|---|
| 3,641,127 | 2/1972 | Farge et al. | 562/426 |
| 3,720,708 | 3/1973 | Halpern | 548/321.1 X |
| 3,896,157 | 7/1975 | Fried et al. | 544/163 X |
| 3,959,364 | 5/1976 | Armitage et al. | 544/59 X |
| 4,894,471 | 1/1990 | Angeletti et al. | 558/378 |

*Primary Examiner*—Joseph Paul Brust
*Attorney, Agent, or Firm*—Mathews, Woodbridge & Collins

[57] ABSTRACT

A process for the α-monoalkylation of arylacetonitriles, arylacetoesters and arylacetic acids with dialkyl carbonates in liquid phase, in the presence of bases at temperatures ranging from about 100° C. to about 270° C.

6 Claims, No Drawings

PROCESS FOR THE ALPHA-MONOALKYLATION OF ARYLACETONITRILES, ARYLACETOESTERS AND ARYLACETIC ACIDS

The present invention relates to a process for the α-monoalkylation of arylacetonitriles, arylacetoesters and arylacetic acids of formula (I), to obtain α-aryl-α-alkyl-acetonitriles or α-aryl-α-alkyl-acetoesters of formula (II), using dialkyl carbonates in liquid phase, according to the following scheme:

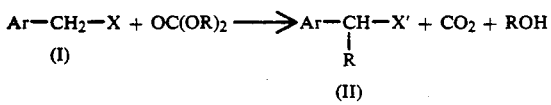

wherein
Ar is an aromatic or hetero-aromatic ring, for example a phenyl, naphthyl, thiophene ring and the like, optionally having one or more substituents, such as $C_1$-$C_4$ alkyl, $C_1$-$C_4$ alkoxy, halogens, carboxy, $C_1$-$C_4$ alkoxycarbonyl, arylcarbonyl, nitrile groups,
X is a CN, COOR or COOH group,
X' is a CN or COOR group,
R is a $C_1$-$C_4$ alkyl group, preferably methyl or ethyl.

The resulting compounds of formula (II) are useful intermediates; in particular, they are useful to prepare, by means of simple hydrolysis of the CN or COOR groups, α-arylpropionic acids, some of which are important from the therapeutical point of view: see, for instance, ibuprofen, naproxen, ketoprofen, fluorbiprofen and the like.

According to the prior art techniques, particularly, the main processes for the preparation of arylpropionic acid comprise: (1) direct or indirect methylation of the corresponding arylacetic acid derivatives; (2) in the case of ketoprofen, introduction of the carbonyl function on the aromatic ring; (3) introduction of the propionic group as such; (4) rearrangements of propiophenones (the relevant literature being extremely wide: see, for instance, U.S. Pat. No. 3,641,127, DOS 2,646,792, DOS 2,744,832, U.S. Pat. Nos. 3,959,364, 3,720,708).

α-Arylpropionic acids (particularly those useful as antiinflammatory drugs), are important from the economic point of view, therefore even complex preparation processes can be industrially interesting, whenever they yield products which are pure or can easily be purified.

The process which is apparently the simplest consists in the selective introduction of a methyl group on the reactive methylene of an arylacetonitrile. Said reaction was studied accurately also under phase-transfer catalysis conditions (M. Mikolajczyk et al., Tetrahedron Lett. 3757 (1975), but it always gave reaction mixtures; in fact, even in the presence of unconverted reagent, the formation of the dimethyl derivative could not be avoided, which makes the separation of the monomethyl derivative difficult and expensive.

On the contrary, no alkylation reactions of arylacetoesters are disclosed: in fact, in this case, the —CH$_2$— group is not acidic enough, therefore the carbanion forms with difficulty, and anyhow the ester will be hydrolyzed under phase-transfer conditions. However, arylacetoesters are known to act as intermediates for the above mentioned antiinflammatory drugs when they are transformed, by means of strong bases, such as sodium hydride, into the corresponding anions which are then treated with methyl iodide. Nevertheless, the monomethylation selectivity is never high: see, for example, monomethylation of methyl (6-methoxy-2-naphthyl)acetate to methyl 2-(6-methoxy-2-naphthyl)propionate (U.S. Pat. No. 3,896,157).

Recently, dialkyl carbonates have been reported to act as alkylation agents on phenols, mercaptans, amines, arylacetonitriles and other CH-acid compounds (P. Tundo et al., Ind. Eng. Chem. Res. 28, 881 (1989)). The reaction is carried out continuously on a column containing catalytic amounts of the base and the phase-transfer catalyst and it proceeds without base consumption since the acidity is removed from the reaction mixture in form of $CO_2$, due to the instability of the O-alkyl-carbonic acids, which represent the leaving group of the dialkyl carbonates during the methylation reaction.

The continuous alkylation of methyl-phenylacetate has also been described (Italian patent appl. n° 20159A/90), but this reaction proceeds markedly more slowly than that to the corresponding nitriles. The reported conversions are of 60% only.

However, continuous reactions in vapour phase, such as those disclosed in EP 240,863 and U.S. Pat. No. 4,894,471, and in Italian Pat. appl. 20159A/90, cannot be used in case of high-boiling products, since such products are difficult to vapourize: the high boiling point of many arylacetonitriles and arylacetoesters can lead to the decomposition thereof, due to the extended time at high temperature on the fix bed in which the reaction takes place.

Now it has surprisingly been found that α-monoalkylation of arylacetonitriles, arylacetoesters and arylacetic acids with dialkyl carbonates proceeds in a highly satisfactory way from the point of view of both selectivity and yields also when such a reaction is carried out in the liquid phase, in batch processes, which obviously do not suffer from the problem of the vapourizing of the high-boiling substrates, which are liable to heat-decomposition. The high selectivity with respect to monoalkyl derivatives achieved by the invention is definitely unforeseeable, since said monoalkyl derivatives, on the contrary to what happens in case of the vapour phase process disclosed in the above cited EP 240,863, U.S. Pat. No. 4,894,471 and It. Pat. appl. 20159A/90, remain for a long time in the reaction medium, in the presence of an alkylating agent and under conditions which are foreseen to be suitable for the formation of the undesired dialkyl derivatives: in fact, a very high selectivity (>99%, as evident from the following examples) is achieved in the presence of a very high dialkyl carbonate excess (from 10 to 50 moles for mole of compound I), which is actually used as the reaction solvent. When X, in formula I, is COOH, the reaction according to the invention occurs with initial formation of arylacetoester Ar—CH$_2$—COOR (U. Romano, Chimica oggi, 1984, 37), which is subsequently mono-alkylated at the α-position.

A further characteristic distinguishing the batch process of the present invention from the one in vapour phase of the prior art resides in the fact that the reaction can be carried out in absence of the phase-transfer catalyst which is essential in the vapour phase. On the contrary, the presence of bases, such as alkali metal carbonates, for example $K_2CO_3$, is necessary. The base amount can range from catalytic to stoichiometric amounts, or even excess amounts to the stoichiometric ratio (related to compound I). Since the temperatures required to obtain good results in "normal" times from the industrial point of view are generally higher than 100° C., and since dimethyl carbonate (DMC) boils under said temperature range, the monomethylation reaction is carried out in apparatuses capable of bearing the required pressures, which, o the other hand, are relatively mild, generally not exceeding 15-25 bars.

It should be noted that monoalkylation of compounds I batchwise, according to the invention, is a much simpler process than that in vapour phase which, as it happens with all the continuous processes, requires a precise optimisation, particularly as far as the flow rate of the reagents is concerned. According to the present invention, on the contrary, it is sufficient to place compound I, the dialkyl carbonate and the base (in a molar ratio from 1:1:0.005 to 1:50:5) in the reactor and to heat the mixture to temperatures ranging from about 100° C. to about 270° C., preferably from about 120° C. to about 250° C., for times varying from about 2 hours to about 40 hours. After that, the reaction mixture can be worked up conventionally, by filtering the solid residue (usually $K_2CO_3$), recovering the dialkyl carbonate excess and isolating the desired product by distillation or crystallization.

The following Examples further illustrate the invention.

EXAMPLE 1

2-(3-Methoxycarbonyl-phenyl)propionitrile

The reaction for the selective methylation is carried out placing into a 250 ml ($\phi_i=45$ mm) stainless steel autoclave a mixture of (3-methoxycarbonylphenyl)acetonitrile (10 g, 96% purity), dimethyl carbonate (86 ml) and $K_2CO_3$ (12 g), in the 1:18:2 molar ratio. Air is replaced by a $N_2$ stream; then the mixture is heated at a temperature of 180° C., with stirring. During the reaction, which is completed within 6 hours, the pressure raises from 7 bars, reached at the working temperature, to about 12 bars after 5 hours of isothermal heating. After cooling $K_2CO_3$ is filtered off, DMC is recovered and the residue is distilled (b.p. 0.078 = 109°-110° C.) to obtain 8.3 g of 2-(3-methoxycarbonyl-phenyl)propionitrile which is 99,5% pure (78% yield) (>99% selectivity in monomethylation).

The same result is obtained, under the same conditions, by decreasing the $K_2CO_3$ amount to 1/10th of that described above.

From the resulting product, the corresponding 3-(1-cyanoethyl)benzoic acid is obtained by means of selective alkali hydrolysis, which is a known intermediate for the preparation of ketoprofen.

EXAMPLE 2

2-(3-Methoxycarbonyl-phenyl)butyronitrile

The procedure of example (1) is followed, using diethyl carbonate instead of dimethyl carbonate. The reaction, which is completed within about 24 hours, takes place at a pressure ranging from 3 bars, which is the value achieved at the working pressure, to about 7 bars.

The title product is obtained in a 80% yield; the monomethylation selectivity being >99%.

EXAMPLE 3

2-(3-Benzoyl-phenyl)propionitrile

A mixture of (3-benzoylphenyl)acetonitrile (1 g), dimethyl carbonate (15 ml) and $K_2CO_3$ (3 g) in the 1:40:5 molar ratio, is reacted in a steel autoclave at the temperature of 140° C. for 10 hours and 30 minutes. After recovering DMC, 0.85 g of the title product are obtained, with a monomethylation selectivity >99% (80% yield), which is hydrolyzed to obtain ketoprofen by known methods.

EXAMPLE 4

2-Phenylpropionitrile

The procedure of example (1) is followed, using phenylacetonitrile, dimethyl carbonate and a catalytic amount of alkali carbonate in a 1:18:0.05 molar ratio. $Li_2CO_3$, $Na_2CO_3$, $K_2CO_3$ and $Cs_2CO_3$ were used respectively, to obtain the following results:

| base | reaction time (h) | conversion (%) | monomethylation selectivity |
|---|---|---|---|
| $Li_2CO_3$ | 7.5 | 5 | |
| $Na_2CO_3$ | 8.75 | 89 | >99% |
| $K_2CO_3$ | 7.5 | 98 | >99% |
| $Cs_2CO_3$ | 5.0 | 99 | >99% |

EXAMPLE 5 a) Monomethylation of methyl (6-methoxy-2-naphthyl)acetate

The reaction for the selective methylation is carried out placing a mixture of methyl (6-methoxy-2-naphthyl)acetate (U.S. Pat. No. 3,896,157; 2 g), dimethyl carbonate (10 ml) and $K_2CO_3$ (0.9 g), in the 1:15:1.5 molar ratio into a 250 ml ($\phi_i=45$ mm) stainless steel autoclave. Air is replaced by a $N_2$ stream; then the mixture is heated to 210° C., with stirring. During the reaction, which is completed within 6 hours, the pressure rises from 18 bars, which are achieved at the working temperature, to about 20 bars after 5 hours of isothermal heating. $K_2CO_3$ is filtered off and the residue is hydrolyzed directly.

Alternatively, the reaction for the selective methylation can be carried out by reacting a mixture of (6-methoxy-2-naphthyl)acetic acid, dimethyl carbonate and $K_2CO_3$, in the 1:20:2 molar ratio, in autoclave at a temperature of 220° C. The reaction is completed within about 8 hours. (In this case DMC acts first as a methylating agent for the carboxylic group, through an already known reaction; then the monomethylation reaction takes place on the resulting ester).

b) Hydrolysis of methyl 2-(methoxy-2-naphthyl)propionate

The reaction product is refluxed in 100 ml of 5% NaOH for 1 hour and 30 minutes. The precipitate is neutralized and filtered, to obtain 1.8 g of Naproxen. Yield (starting from the not methylated ester): 90%.

EXAMPLE 6

Flurbiprofen

Following the procedure of example (5), a mixture of 2 g of methyl (2-fluoro-4-biphenyl)acetate (U.S. Pat. No. 3,755,427), 14 ml of dimethyl carbonate and 1.7 g of $K_2CO_3$, in a 1:20:1.5 molar ratio, is reacted in autoclave at a temperature of 210° C.; the reaction is completed within 6 hours. The resulting product, methyl α-(2-fluoro-4-biphenyl)propionate, is hydrolyzed with 100 ml of 5% NaOH, as in example 5, to give α-(2-fluoro-4- biphenyl)propionic acid (Flurbiprofen) with 100 ml of 5% NaOH, as in example 5. Yield (starting from the not methylated ester): 85%.

EXAMPLE 7

Ibuprofen

Following the procedure of example 1, a mixture of 2 g of methyl (4-isobutylphenyl)acetate (EP 347,939), 16 ml of dimethyl carbonate and 2 g of $K_2CO_3$, in a 1:20:1.5 molar ratio, is reacted in autoclave at a temperature of 210° C. The reaction is completed within about 8 hours. The product, methyl α-(4-isobutylphenyl)propionate, is hydrolyzed to α-(4-isobutyl)propionic acid (Ibuprofen) as in the examples above. Yield (starting from the not methylated ester): 90%.

EXAMPLE 8

α-Phenylpropionic acid

Following the procedure of examples 5-7, a mixture of 2 g of methyl phenylacetate, 23 ml of dimethyl carbonate, 2.8 g of $K_2CO_3$, in a 1:20:1.5 molar ratio, is reacted in autoclave at a temperature of 210° C. for 8 hours. The product, methyl α-phenylpropionate, is hydrolyzed to α-phenylpropionic acid according to the procedure of example 5. Yield 85%.

α-Phenylmethylpropionate can be obtained under similar conditions, by reacting a mixture of phenylacetic acid, dimethyl carbonate and $K_2CO_3$, in a 1:20:2 molar ratio, in autoclave at a temperature of 225° C., for 15 hours.

EXAMPLE 9

Ethyl α-phenylbutyrate

A mixture of 2 g of ethyl phenylacetate, 30 ml of diethyl carbonate, 2.5 g of $K_2CO_3$, in the 1:20:1.5 molar ratio, is reacted in autoclave at 225° C. After 14 hours, a 30% conversion is achieved, with formation of ethyl α-phenylbutyrate as the mono-C-ethylation product.

We claim:

1. Process for the preparation of an α-substituted compound of the formula:

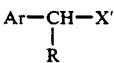

in which
Ar is phenyl, naphthyl, or thienyl, each of which is unsubstituted for substituted with alkyl of 1 to 4 carbon atoms, alkoxy of 1 to 4 carbon atoms, halo, carboxy, alkoxycarbonyl of 1 to 4 carbon atoms in the alkoxy group, arylcarbonyl, or cyano,
X' is —CN or —COOR, and
R is alkyl of 1 to 4 carbon atoms,
which comprises heating a reaction mixture consisting essentially of
(i) an acetic acid derivative of the formula:

in which Ar is as previously defined and X is —CN, —COOH, or —COOR, in which R is as previously defined,
(ii) from 1 to 50 molar equivalents, per mole of acetic acid derivative, of a dialkyl carbonate of the formula ROCOOR, in which R is as previously defined, and
(iii) from 0.005 to 5 molar equivalents, per mole of acetic acid derivative, of a base,
in liquid phase at temperatures of from about 100° C. to about 270° C.

2. The process according to claim 1 wherein the dialkyl carbonate is dimethyl carbonate.

3. The process according to claim 1 wherein the dialkyl carbonate is diethyl carbonate.

4. The process according to claim 1 wherein the base is an alkali earth metal carbonate or bicarbonate.

5. The process according to claim 1 wherein the reaction mixture is heated at temperatures of from about 120° C. to about 250° C.

6. The process according to claim 1 wherein Ar is phenyl, 3-methoxycarbonylphenyl, 3-benzoylphenyl, or 6-methoxynaphth-2-yl.

* * * * *